United States Patent [19]

Charm

[11] Patent Number: 4,975,246
[45] Date of Patent: * Dec. 4, 1990

[54] HIGH TEMPERATURE, SHORT TIME HEATING SYSTEM AND METHOD OF HEATING HEAT-SENSITIVE MATERIAL

[76] Inventor: Stanley E. Charm, 10 Rowes Wharf, Boston, Mass. 02110

[*] Notice: The portion of the term of this patent subsequent to Jun. 13, 2006 has been disclaimed.

[21] Appl. No.: 300,966

[22] Filed: Jan. 23, 1989

Related U.S. Application Data

[63] Continuation-in-part of Ser. No. 71,733, Jul. 8, 1987, Pat. No. 4,839,142, which is a continuation-in-part of Ser. No. 782,019, Sep. 30, 1985, abandoned.

[51] Int. Cl.$^5$ .................... A61L 2/12; C07K 3/12
[52] U.S. Cl. .................... 422/21; 426/241; 426/521; 426/522; 435/2; 530/363; 530/380; 530/383
[58] Field of Search .................... 422/21, 307; 530/363, 530/380, 383; 426/234, 241, 243, 521, 522; 219/10.55 F, 10.55 R, 10.55 A, 10.55 M; 210/748, 764, 774, 177, 181, 182; 435/2

[56] References Cited

U.S. PATENT DOCUMENTS

| | | |
|---|---|---|
| 1,863,222 | 6/1932 | Hoermann . |
| 2,333,842 | 11/1943 | Cascio et al. .................... 250/49.5 |
| 3,256,101 | 6/1966 | Arns .................... 426/241 |
| 3,296,122 | 1/1967 | Karassir et al. .................... 210/181 |
| 3,439,510 | 4/1969 | Gray .................... 62/78 |
| 3,492,212 | 1/1970 | Searcy .................... 204/160.1 |
| 3,494,726 | 2/1970 | Gray . |
| 3,535,482 | 10/1970 | Kluck .................... 219/10.55 |
| 3,579,631 | 5/1971 | Stewart, Jr. et al. .................... 426/521 |
| 3,623,894 | 11/1971 | Lund .................... 426/522 |
| 3,660,234 | 5/1972 | Gray .................... 424/89 |
| 3,676,058 | 7/1972 | Gray . |
| 3,706,631 | 12/1972 | Falk . |
| 3,764,009 | 10/1973 | Watt .................... 210/177 |
| 3,809,845 | 5/1974 | Stenstrom .................... 422/21 |
| 3,934,042 | 1/1976 | DeStoutz .................... 426/522 |
| 4,251,437 | 2/1981 | Rasmussen et al. . |
| 4,260,490 | 4/1981 | Moss et al. . |
| 4,366,051 | 12/1982 | Fischel .................... 210/181 |
| 4,393,088 | 7/1983 | Matsusaka .................... 426/234 |
| 4,395,397 | 7/1983 | Shapiro .................... 424/101 |
| 4,613,501 | 9/1986 | Horowitz .................... 435/238 X |
| 4,720,385 | 1/1988 | Lembach .................... 530/380 X |
| 4,727,027 | 2/1988 | Wiesrhahn et al. .................... 530/380 X |

Primary Examiner—Robert J. Warden
Assistant Examiner—Jill Johnston
Attorney, Agent, or Firm—Richard P. Crowley

[57] ABSTRACT

A high temperature, short time heating system and method for the pasteurization and/or sterilization of heat-sensitive material to destroy substantially selected pathogenic microorganisms without substantially affecting other desirable properties of the material, such as proteinaceous matter, which method comprises: subjecting the material to microwave energy to heat rapidly the material for a short time period to a pasteurizing or sterilization temperature for a short holding time period; rapidly cooling the heated material; and recovering an aseptic biological fluid.

43 Claims, 3 Drawing Sheets

HIGH TEMPERATURE, SHORT TIME HEATING SYSTEM AND METHOD OF HEATING HEAT-SENSITIVE MATERIAL

REFERENCE TO PRIOR APPLICATIONS

This application is a continuation-in-part application of U.S. Ser. No. 071,733, filed July 8, 1987 now U.S. Pat. No. 4,839,142, issued June 13, 1989 which was a continuation-in-part application of U.S. Ser. No. 782,019, filed Sept. 30, 1985, now abandoned.

BACKGROUND OF THE INVENTION

It is often desirable, particularly in the food industry, to preserve heat-sensitive foods, such as milk or goods with delicate flavor components, by heating such heat-sensitive foods to high temperatures for very short periods of time, as in pasteurization and sterilization of food products. However, many such systems are available only for relatively large scale food productions and do not permit small scale laboratory productions or experiments with valuable, low volume material, such as heat-sensitive biological fluids or suspensions, used in the laboratory, such as fermentation media, vaccines, liposomes and cell culture media. At present, the primary commercial method to remove microorganisms from heat-sensitive liquid material is the use of ultrafiltration to affect a 6-log reduction of the bacteria.

Further, it is often desirable to pasteurize biological fluids or suspensions, such as plasma or protein-containing fluids, to destroy selected pathogenic organisms, such as infectious agents like a virus or other agent compound substantially of protein and nucleic acids, without destroying or substantially altering other microorganisms or precipitating or destroying other proteinaceous matter material. For example, it is desirable to destroy selectively virus and virus-type agents from blood plasma or serum without clotting, clouding, aggregating, coagulating, precipitating or biologically altering the plasma in the process.

Therefore, it is desirable to provide for a continuous, fast, heat processing apparatus and a method for the high temperature, short time heating, for example, to provide sterilization or pasteurization of heat-sensitive fluids, including body fluids, particularly for use with low volume biological fluids and for small scale laboratory use.

SUMMARY OF THE INVENTION

The invention relates to a heat processing apparatus and system and to a method for the high temperature, short time heating of heat-sensitive material. In particular, the invention concerns a microwave-based heat processing system and a method for the high temperature, short time, rapid heating of heat-sensitive, liquid, biological fluids employing microwave energy and rapid cooling of the heated fluid.

The present invention permits the continuous, rapid heating of the heat-sensitive material so as to effect heating, such as sterilization or pasteurization, without destroying or substantially altering biological activity, flavor or other desirable properties of the heat-sensitive material, but permits the selected destruction of microorganisms. The apparatus and method are particularly useful for, but not limited to: small scale laboratory production or experiments with valuable, low volume biological fluids or other materials and also the selective destruction of infectious agents, like viruses and virus-type agents, from fluids, like body fluids, such as blood plasma.

The method of the invention comprises employing microwave or other rapid heating energy, such as derived from a microwave oven or generator, as a microwave source to heat a heat-sensitive fluid rapidly at a very high rate, for example 25° C. to 8000° C. per second, typically 50° C. per second or more, e.g. 50° C. to 4000° C. per second, for a short heating time period to a defined, selected temperature. The selected temperature, for example, may be a sterilization temperature of 143° C. or more, or a pasteurization temperature, for example, of 60° C. to 95° C. or more. The method includes holding the heated fluid at that temperature for a selected holding time period of about 0.1 seconds or less to affect the destruction of the desired microorganisms. The method also includes as an essential step thereafter rapidly cooling the heated fluid for example at a rate of 100° C. per second or more, e.g. 200° C. to 1000° C. per second to a selected lower temperature, for example, below 40° C., such as 4° C. to 30° C. The method comprises circulating the heat-sensitive liquid material during the heating, holding and cooling time periods.

It is essential to affect the substantial destruction of pathogenic microorganisms or viruses in a heat-sensitive liquid without the substantial destruction of other desirable activities, properties or components of the heat-sensitive, liquid material. In the method, the heat-sensitive, liquid material must be rapidly heated at a high heating rate and rapidly cooled at a high cooling rate and held at a selected temperature for a very short holding time period, typically less than 100 milliseconds. The high rate of heating to a selected holding temperature for a short holding time period and a high rate of cooling thereafter is essential to the method. It has been discovered that at defined lower temperatures, for example, generally below 50° C. to 60° C., the desirable materials, such as proteinaceous material, in the heat-sensitive liquid are destroyed at a faster rate than the microorganism, for example, the bacterial phage material or virus. At higher temperatures, typically temperatures greater than about 60° C. to 65° C., the virus or microorganism material is typically destroyed at a faster rate. Therefore the heat-sensitive material is rapidly heated, preferably by microwave energy, held at a selected holding temperature, which temperature is above the defined temperature wherein the rate of destruction of the heat-sensitive versus the microorganism or virus changes for a time, such as about 0.100 seconds or less, and then rapidly cooled to a temperature where considerably reduced or no destruction of the heat-sensitive material occurs. The heating time to heat the heat-sensitive material to the holding temperature can constitute up to 20% of the total lethability or kill of the microorganisms or viruses.

The total time period for the heating, cooling and holding should be as short as possible and generally less than 1 to 2 seconds in total, and more particularly, generally less than 0.1 or 0.05 seconds. The selected temperature for destruction is generally more than about 60° C., that is, in a pasteurization process where a 6-log reduction is desired, it often ranges from 65° C. to 95° C. to affect pasteurization of the heat-sensitive, liquid material, which corresponds with a 99.9999% destruction of the microorganisms or viruses. This level of reduction is generally accepted for commercial sterile filtration processes. However, the method can be carried out at higher temperatures, that is, at sterilization temperatures, where a higher-log reduction occurs, such as 12-log reduction at 143° C., or any desirable degree of reduction of microbial spores as required.

The method comprises rapidly heating, preferably by microwave energy, a heat-sensitive material which contains proteinaceous material and one or more pathogenic microorganisms, at least one of which microorganisms is desired to be reduced, that is, killed, by heat in a selected time period. The selected temperature is above the temperature at which the rate of destruction of the microorganisms or viruses to be destroyed is greater than the rate of destruction of the heat-sensitive material. The heat-sensitive material is then held at a selected holding temperature for a short time period, but sufficient to affect the desired degree of destruction of the microorganisms or viruses. Thereafter the heated material is rapidly cooled to a temperature wherein the rate of destruction of the proteinaceous material is nonexistent or low, for example, generally less than 30° C., which may range from 0° C. to 30° C. During the heating, holding and cooling periods, the heat-sensitive material is generally circulated through a flow path, such as a tubing of defined dimensions such as plastic tubing, said tubing passing through the heating source. Thereafter directly through the cooling source, such as vacuum coolers or heat exchangers, where metal tubing may be used to increase the cooling rate. Where microwave energy is employed as a source of rapid heating, then the tubing is microwave permeable. Optionally, where required, a dielectric-enhancing additive may be added to the fluid to increase the heating rate.

The method of the invention comprises the subjecting of a heat-sensitive biological fluid, such as, but not limited to, blood plasma or serum containing a virus, to microwave energy, typically by the employment of a commercial or industrial microwave generator. The amount of microwave power to be used may vary as desired and, for example, may range from 500 to 6000 watts or higher or lower and contains a microwave permeable zone, e.g. of plastic or glass tubing therein, through which the heat-sensitive solution is circulated for a selected period of time to achieve sterilization or pasteurization temperatures. For higher flow rates, microwave generators with higher power capacity may be used.

In one embodiment, since the heating time in a microwave source depends on the dielectric constant of the material, a dielectric constant enhancing additive is employed and added to the heat-sensitive material to adjust the dielectric constant to provide the short heat time period. The enhancing additive must be dissolved in the material. The additive is of a type and added in an amount sufficient to provide for enhanced dielectric constant of the fluid, so that the biological fluid may be rapidly heated by the microwave energy in a short time period. The dielectric constant additive should not affect the desired essential nature or quality of the material to which it is added, i.e. should be biologically inert. The additive may comprise a high dielectric salt or salt solution, and typically an inorganic metal or ionic salt, such as an alkali or alkaline earth salt, with sodium chloride, one preferred additive for blood plasma. Typically, the additive is added to the biological fluids in an aqueous solution. Where the biological fluid already has a high dielectric constant, an additive need not be employed. The liquid material, including suspension, are circulated by pumping, typically through plastic or glass tubing extending through the rapid heating source, such as the microwave oven or waveguide, so that the material may be rapidly heated to the selected sterilization or pasteurization temperature. The heated heat-sensitive material is then rapidly cooled, typically while being circulated through the cooling system, such as a vacuum cooler, and optionally, the dielectric additive is then removed, if added, and the cooled, aseptic material recovered.

The method and system may be used to sterilize or pasteurize a wide variety of materials including, but not limited to: food products, such as liquid egg products; biological fluids, such as microbiological media; tissue culture media; suspensions that cannot be sterilized or pasteurized employing ultrafiltration, such as liposomes or collagens; vaccines; mother's milk; fermentation media and cell culture media. Also, drugs encapsulated in liposomes or other heat-sensitive suspensions can be pasteurized or sterilized without substantially affecting the drug activity. The method may also be used to pasteurize blood plasma (whole plasma or serum) and blood plasma products containing Factors VIII, IX and Immunoglobulins and to destroy selectively agents likes viruses and mycoplasma, such as those causing hepatitis, AIDS and the like. In one embodiment, the system is designed to accommodate flow rates generally of from about 3 liters per hour or more, e.g. 3 to 25 liters per hour, with a hold-up volume of about 0.5 liters or less. In another embodiment, the hold up volume may be 0.5 ml with a flow rate of 3 to 15 liters per hour which is a particularly useful system for testing expensive, heat-sensitive fluids.

The system employs a microwave power source and the necessary instrumentation to maintain sufficient back-up pressure to permit a temperature of the fluid in the oven, e.g. of greater than 60° C., that is, selected sterilization or pasteurization temperature or such other predetermined temperature. The heating, holding and cooling times totalling 2 seconds or less at the sterilization temperature of 143° C. are typically sufficient to achieve sterility as defined by the 12-log reductions of a heat-resistant bacterial spore, such as Cl botulinum. It has been found that a total heating, holding and cooling time of less than about 0.5 seconds with a peak temperature of 80° C. is generally sufficient to achieve a 6-log cycle reduction of bacteria, such as $E.\ coli$ or viruses.

Since the heating-up time of the fluid in the microwave oven depends on the dielectric constant of the material being heated, where required, the dielectric constant enhancing additive is added in various amounts as required, such as sodium chloride or other inert, pharmaceutically inactive salt or salt solutions, more typically as a saline solution. While the amount of the dielectric constant enhancing additive may vary depending on the dielectric constant of the original biological fluid, generally from about 0.1 to 10 percent or more by weight of the fluid of a salt may be added, 0.5 to 4.0 percent, and even more particularly 0.05 to about 1.5 percent, is often sufficient to enable rapid sterilization using a commercial microwave oven or industrial microwave generator. Excessive quantities of the dielectric constant enhancing additive should be avoided, since optionally the additive should be removed from the sterilized biological fluid. The biological fluid with the additive may vary in dielectric constant depending on the desired temperature to be reached, but generally the biological fluid with the additive should have a dielectric constant of at least that of water, such as from about 90 to 300, such as about 100 to 200.

The size of the tubing in the microwave heater, usually in coiled or serpentine form, employed must hold up sufficient volume within the microwave chamber so that sufficient microwave energy will be absorbed. A higher dielectric constant biological fluid will of course require a smaller hold-up volume than a lower dielectric constant material. Therefore, where adjustment of a dielectric constant cannot be entirely made employing a dielectric constant enhancing additive, varying tubing size for circulating the biological fluids through the microwave oven should be used to accommodate different ranges of dielectric constant fluids.

The heat-sensitive material is generally circulated through tubing in the microwave heater by a pump. Also, a back pressure valve is typically employed after the cooler to prevent flashing of the fluid or vaporization of the heated material, and a divert valve is employed after the cooling mechanism so that any biological fluid which does not reach the necessary selected sterilization temperature may be diverted and discarded. Also, generally where the dielectric constant enhancing agent is added, it is desirable to remove such enhancing agent from the sterilized biological fluid under aseptic conditions, such as by the employment of ultrafiltration, dialysis or chromatography columns or other salt separation techniques. Thus, the dielectric constant enhancing agent, where applicable, should also be selected for easy or effective removal or separation from the sterilized or pasteurized biological fluid prior to recovery of the biological fluid in a receiver. Optionally, with certain products, such as blood clotting factors, may be removed from blood plasma after the short time heating process and the removal of the dielectric enhancer, e.g. salt, may be unnecessary.

The heat processing system of the invention comprises: a source of heat-sensitive material to be heated; optionally means to provide for the addition of a sufficient amount of a dielectric constant enhancing agent to the material; means to circulate, such as by pumping, the material during the time of exposure to the microwave energy through a microwave permeable container, such as tubing, at a desired length and diameter through a microwave source, such as a commercial microwave oven, for a defined hold-up time and through the cooling means; a cooling means, such as a cooler, to cool rapidly the heated, processed material to a lower temperature, such as below 40° C. or lower; a back pressure valve means to prevent the vaporization of the heated material; optionally, but preferably, a divert valve means so that the heated material that is not at the desired sterilizing or pasteurizing temperatures may be diverted; optional separating means to remove the dielectric constant enhancing agent from the sterilized material under sterile conditions; and an aseptic receiver to receive the heat-sterilized material. Optionally, the material diverted may be recycled to the source, and of course, where employed, the inert dielectric constant enhancing agent also may be recycled for further use with the material after removal.

The invention will be described for the purposes of illustration only in connection with certain embodiments; however, it is recognized that various changes, additions and improvements may be made in the invention by those persons skilled in the art, without departing from the spirit and scope of the invention.

DESCRIPTION OF THE EMBODIMENTS

Figure 1:
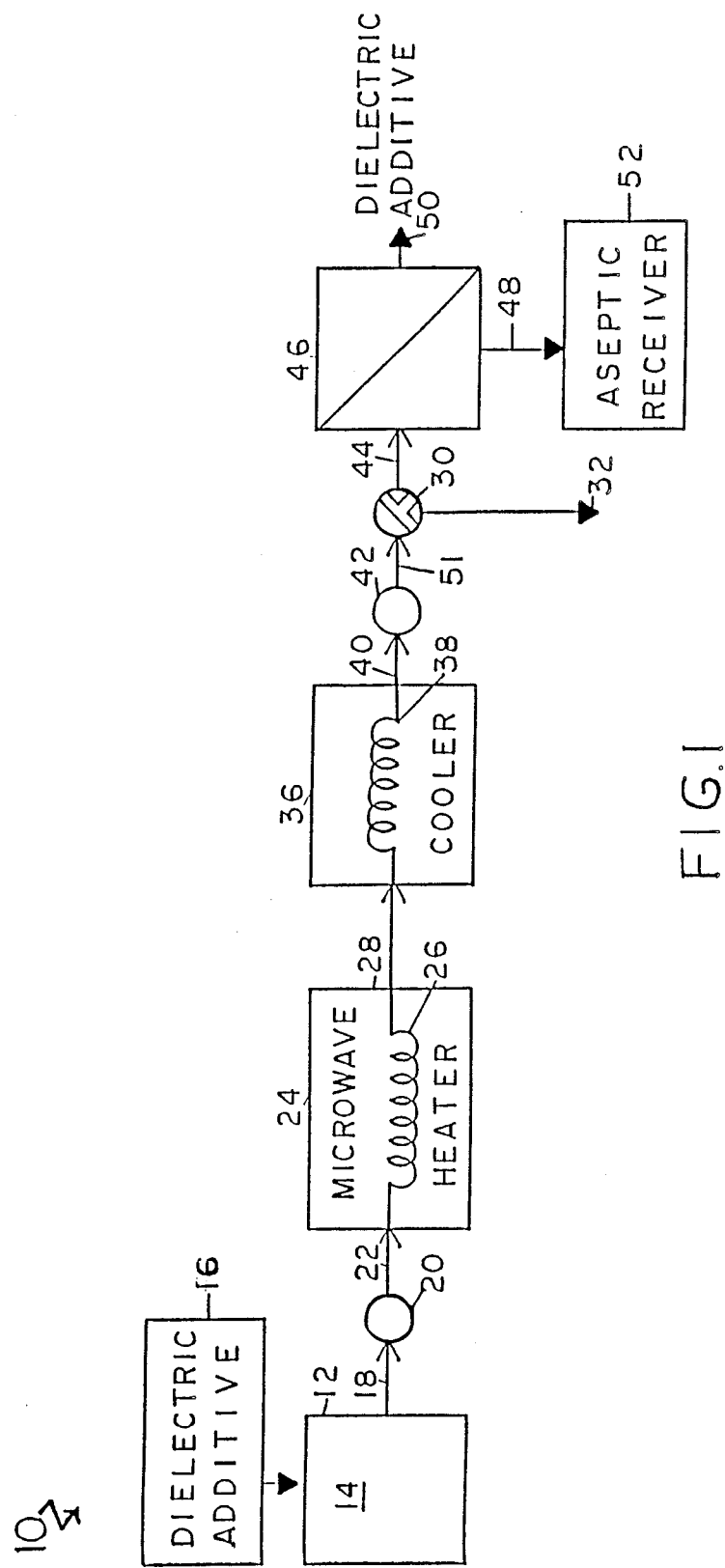
FIG. 1 is a schematic, illustrative drawing of a heat processing system employing the method of the invention.

FIG. 1 shows a heat processing system 10 comprising a container 12 containing a heat-sensitive biological fluid 14 and a source of a dielectric additive 16, such as a sodium chloride solution, which is added to the heat-sensitive biological fluid 14. The biological fluid 14 with the dielectric additive is then introduced through line 18 through pump 20 and line 22 into a microwave heater 24 wherein a defined volume of the biological fluid is present in the plastic tubing 26 and subject to microwave energy wherein the biological fluid now at a high dielectric constant is heated at a high rate, 50° C. per second or more, for about 3.0 seconds or less, to 160° C. The heated fluid is then withdrawn through line 28. The fluid is held at the high temperature for a holding time period of 0.1 seconds or less in line 28. The biological fluid is then introduced into a metal tube 38 in a cooler 36 where it is cooled rapidly to room temperature, for example 20° C. or below, and then introduced through line 40 through a back pressure valve 42 which prevents the vaporization of the heated fluid. The heated fluid is then withdrawn through line 51 through a divert three-way valve (divert/non-divert) 30. If the biological fluid does not reach the heat sterilizing or pasteurizing temperature, the biological fluid is diverted through line 32 and discarded. The heated fluid may then be introduced through line 44 into a separator 46, such as a dialysis unit or chromatography column, ultrafiltration or other separation means, and all or some of the added dielectric additive is then removed through line 50 and the sterilized biological fluid is removed through line 48 into an aseptic receiver 52 for laboratory, experimental or other use.

Figure 2:
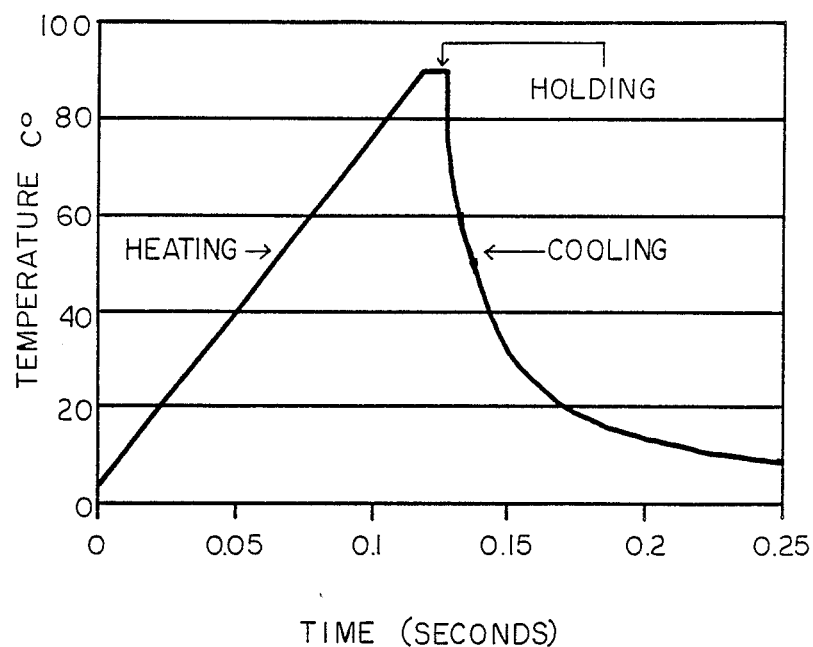
FIG. 2 is a time-temperature graph representing data of the pasteurization of a heat-sensitive material containing a bacteria.

FIG. 2 is a time versus temperature graph representing the data obtained by Example 8 and illustrating the pasteurization of a heat-sensitive material containing a contaminating microorganism. The tubing employed in the heating, holding and cooling sections had the same diameter with the heating section 53.3 cm, the holding section 3.6 cm and the cooling section 43.1 cm. The heating time was 0.1188 seconds, the holding time 0.0079 seconds and the cooling time 0.095 seconds for a total time period of less than 250 milliseconds. The cooling curve has a log shape due to the conductive heat transfer in the cooling heat exchanger.

Figure 3:
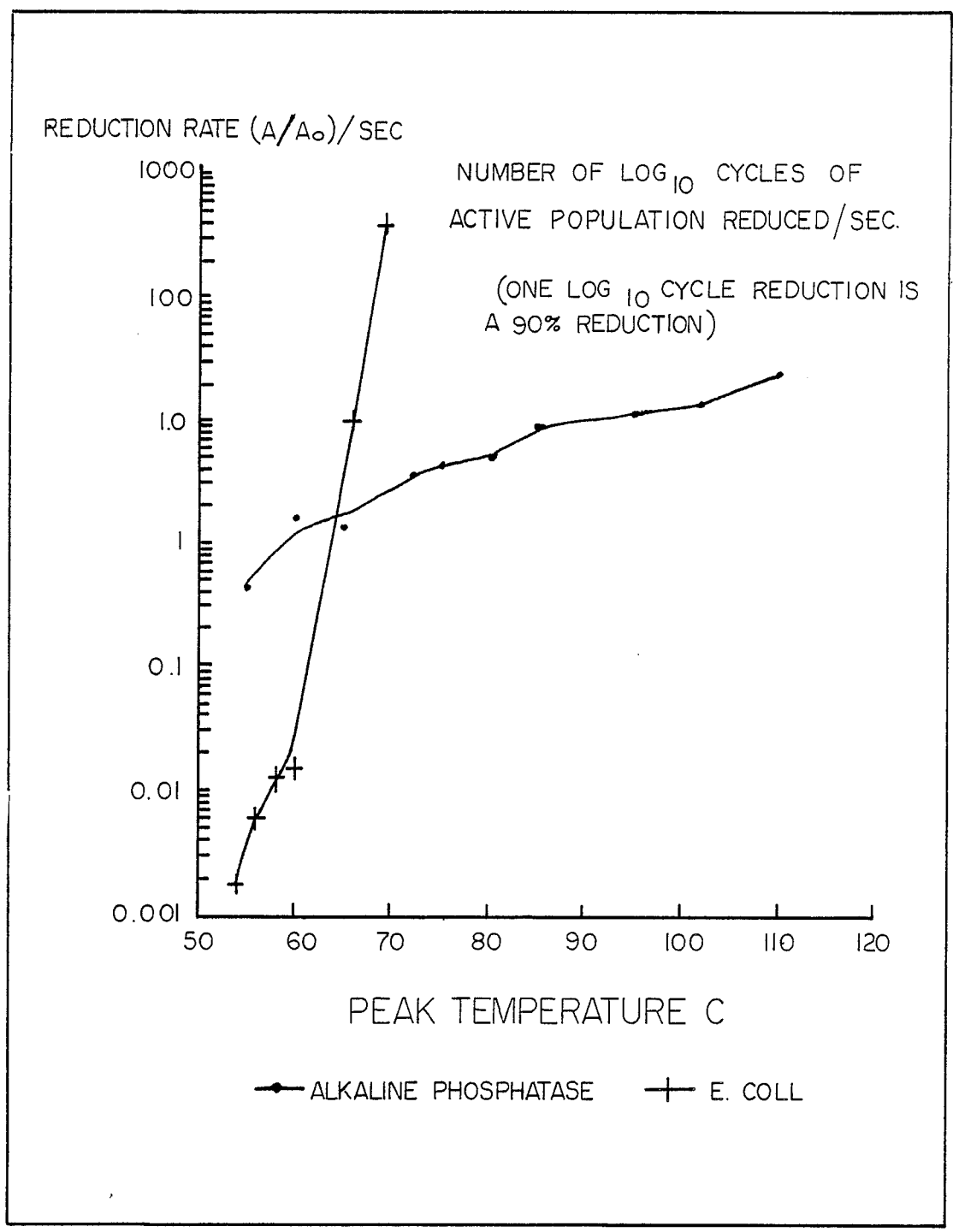
FIG. 3 is a bacteria log reduction-rate versus temperature graph representing data of the reduction rate of bacteria with peak temperature.

FIG. 3 is a rate of reduction versus temperature graph of experimental data which illustrates the principal of the invention. A heat-sensitive, aqueous liquid sample material was prepared employing *E. coli* as a sample microorganism and the enzyme alkaline phosphatase as the heat-sensitive material. The X-axis of the graph shows the peak temperature at which the heat-sensitive material was held during the microwave pasteurization process, while the Y-axis is the number of $\log_{10}$ cycles of the *E. coli* inactivated or reduced per second. As shown at the higher temperatures of 80° C.

and above, the rate of reduction of the *E. coli* microorganism is much greater than the rate of inactivation of the heat-sensitive enzyme.

EXAMPLE 1

Certain tests were conducted employing saline solutions of various weight percent salt with an initial temperature of about 27° C. and a resulting cooled temperature of about 4° C. employing the apparatus as described in the drawing with the test results as set forth in the accompanying table.

As illustrated, the saline solutions of 0.9 and 1.5 percent, in contrast to the lower dielectric constant saline solution of 0.5 percent, provide for a very rapid increase in temperature in less than 6 seconds to the sterilization time and temperature of 143° C. and for a holding time of one-half of a second, all with substantially the same flow rates. The use of a 4 percent saline solution provides for a more rapid temperature rise and short time, 0.15 seconds, at a sterilization temperature of 143° C. to 144° C.

EXAMPLE 2

A heat-sensitive biological fluid comprising blood plasma to which has been added 4 weight percent sodium chloride was processed in the apparatus of the drawing, but without the removal of the salt, with the results shown in Table II.

TABLE I

| | Saline Solution | | | |
|---|---|---|---|---|
| Weight Percent Salt | Heating Time (seconds) to 143° C. | Holding Time (seconds) at 143° C. | Cooling Time (seconds) | Flow Rate L/hr |
| 0.5 | 16 | 0.5 | 2.5 | 3.6 |
| 0.9 | 6 | 0.5 | 2.5 | 3.3 |
| 1.5 | 5 | 0.5 | 2.5 | 3.3 |
| 4.0 | 3.5 | 0.15 | 2.5 | 3.3 |

In Example 2, there was no change in albumin, globins or Factors VIII and IX in comparison to an unprocessed control sample. Example 2 demonstrates that heat-sensitive blood plasma containing pathogenic viruses, such as hepatitis B or AIDS, may be pasteurized with the destruction of the viruses by the rapid high temperature microwave heating method. As illustrated, the pasteurization holding time with the addition of the dielectric additive is very short, 0.05 to 0.07 seconds, to provide heating without affecting clotting factors unless the heating time is more than 1.9 seconds with a holding time of 0.07 seconds.

EXAMPLE 3

Blood plasma has been processed in the prior art at temperatures of 59° C. for a time period of 12 hours in an attempt to destroy viruses and yet to preserve the blood clotting factors of the blood plasma, e.g. Factors VIII and IX; however, the hepatitis B virus and other agents can survive this process. Further, the process is time consuming. It has been found possible to achieve high temperatures, e.g. 75° C. or more, for short time periods, e.g. for 0.5 seconds or less, such as 0.05 seconds, employing microwave energy and still preserve the blood clotting factors in the blood plasma while destroying by the short heating time infectious agents, such as viruses. By achieving temperatures and times in the range of 75° C. for 0.05 seconds, it is possible to preserve Factors VIII and IX in blood plasma with 4 percent salt in the plasma and to destroy viruses in the plasma.

In determining the amount of dielectric additive necessary to be added, a measure of the dielectric constant may be obtained by passing the liquid at a rate of 8.35 liters/hour through 28 feet of 1/16″ I.D. tubing spaced throughout the volume of the microwave heater and allowing the system to come to a steady state. The liquid residence time in microwave is 7.04 seconds.

As illustrated by the test data in Table III, the increase in temperature rise is associated with an increase in dielectric constant (water having a dielectric constant of about 69 and 4 percent salt solutions about 126).

TABLE II

| | 4 Percent Salt Blood Plasma Fluid | | | |
|---|---|---|---|---|
| Final Temperature (°C.) | Heating Time (seconds) | Holding Time (seconds) | Cooling Time (seconds) | Remarks |
| 68 | 1.5 | 0.05 | 0.9 | No clotting |
| 71 | 1.75 | 0.06 | 1.1 | No clotting |
| 76 | 1.9 | 0.07 | 1.2 | No clotting |
| 81 | 2.1 | 0.07 | 1.3 | Clotting |
| Flow Rate: | | | 3.3 L/hr | |
| Microwave Oven Power: | | | 700 watts | |
| Hold-up Volume in Microwave: | | | 40 ml | |

TABLE III

| Material | Initial Temperature (°C.) | Final Temperature (°C.) | Difference (°C.) | Percent Change From Water |
|---|---|---|---|---|
| Water | 25.6 | 62.2 | 36.6 | — |
| 0.5% Salt | 25.0 | 72.8 | 47.8 | +30.6 |
| 1.0% Salt | 22.8 | 78.3 | 55.5 | +51.6 |
| 2.0% Salt | 23.9 | 85.0 | 61.1 | +66.9 |
| 4.0% Salt | 25.0 | 91.7 | 66.7 | +82.2 |
| 10.0% Salt | 28.3 | 98.3 | 70.0 | +91.3 |
| 20.0% Salt | 22.2 | 95.0 | 72.7 | +98.6 |

EXAMPLE 4

A heat-sensitive biological fluid comprising DMEM tissue culture media with 10% fetal bovine serum had T4 coliphage added. T4 coliphage is a bacterial virus. The media was processed (pasteurized) in the apparatus of the drawing. No salt was added or removed because the DMEM media had a high dielectric constant due to ionic material originally in the DMEM. The biological solution was tested for presence of T4 coliphage and for concentration of protein in the solution. At 93° C., all the T4 coliphage is destroyed, and the biological fluid retains biologically active proteins.

EXAMPLE 5

A solution of *Staphylococcus aureus* bacteria suspended and grown is a fermentation broth of yeast extract, casein hydrolysate and glucose which was processed (sterilized) in the apparatus of FIG. 1.

These experiments indicate the sterilization by the apparatus is more effective than chemical sterilization in this application.

EXAMPLE 6

An artificial blood component consisting of hemoglobin encased in liposome vesicles was suspended in 0.9% weight/volume sodium chloride solution. The solution was processed in the apparatus of the drawing.

TABLE VI

| | |
|---|---|
| Initial Temperature: | 4° C. |
| Heating Time | 1.4 seconds |
| Holding Time | 0.008 seconds |
| Cooling Time | 2.55 seconds |
| The solution was heated to a final temperature of 75° C. | |

The solution was tested and found the integrity of the hemoglobin protein was maintained.

TABLE IV

| Initial Temperature (°C.) | Heating Time (seconds) | Holding Time (seconds) | Cooling Time (seconds) | Final Temperature (°C.) | Concentration of T4 Coliphage (units/ml) | Comments |
|---|---|---|---|---|---|---|
| 20 | 1.4 | 0.01 | 2.55 | 61 | $4.3 \times 10^{10}$ | No reduction of phage |
| 20 | 1.4 | 0.01 | 2.55 | 78 | $3.4 \times 10^{10}$ | Slight reduction of phage |
| 20 | 1.4 | 0.01 | 2.55 | 93 | None | All T4 Coliphage Destroyed |

Initial concentration of T4 Coliphage = $1.7 \times 10^9$ units/ml

TABLE V

| Initial Temperature (°C.) | Heating Time (seconds) | Heating Temperature (°C.) | Holding Time (seconds) | Cooling Time (seconds) | Sterile | Protein A Binding To $I_gG$ Antibodies |
|---|---|---|---|---|---|---|
| *5 | 2.8 | 160 | 0.016 | 3.2 | Yes | Greater than 2.5 mg/10% solution |
| **5 | 0 | 0 | 0 | 0 | Yes | (0.8 to 1.8 mg)/10% solution |

*Samples were collected aseptically and tested for sterility and Protein A activity.
**Previous method of sterilization by chemical inactivation. This sample not heated at all.

TABLE VII

| Solution Rate (°C./second) | Temperature In (°C.) | Temperature Out (°C.) | Flow (L/hr) | Heating Rate (°C./second) |
|---|---|---|---|---|
| .9% NaCl | 23 | 140 | 25.2 | 3046 |
| .1% NaCl | 24 | 170 | 42 | 6335 |
| Tap Water | 35 | 125 | 41.7 | 3877 |

Length of tubing in microwave = 3 cm

EXAMPLE 7

A different higher heating rate was obtained by using an industrial microwave source to heat the biological solutions. This system reduces the length of tubing inside the microwave field therefore increasing the heating rate of the fluid. The system was tested using different salt water solutions. With the industrial microwave generator it was not necessary to change the length of tubing in the heating chamber. The dielectric constant change in solution is compensated for by a tuning circuit in the microwave chamber.

EXAMPLE 8

The described apparatus without the addition of a dielectric additive has been used to pasteurize a preparation of 5% IgG (Immunoglobulin) solution, derived from human plasma with the results shown in Table VIII and the heating, cooling and holding time periods shown in FIG. 2.

The physical integrity of the IgG is measured using High Pressure Liquid Chromatography. The percent of total IgG which have formed aggregates is an indication of this destruction. The IgG is considered good if the aggregation is less than 2.0%.

TABLE VIII

| | |
|---|---|
| Heat Sensitive Material: | Concentrated IgG protein 5% wt/vol in pH 5.3 Phosphate Buffer |
| Flow Rate: | 8 L/Hr |
| Reynolds Number: | 9065 (Turbulent Flow) |
| Microorganism: | E. coli |

| Pasteurization Temperature | IgG Percent Aggregation | E. coli Log Reduction |
|---|---|---|
| 65° C. | 0.38% | 0.08 |
| 77° C. | 0.62% | 5.04 |
| 79° C. | 1.24% | 7.55 |
| 85° C. | 6.12% | 9.20 |

EXAMPLE 9

Currently, products made from raw eggs must be frozen to prevent growth of bacteria which is in most eggs in small amounts. With the described device, the egg product can be heat processed destroying contaminating, non-spore-forming microorganisms. Many pathogenic microorganisms are non-spore-forming, e.g. salmonella. The product can be stored at refrigerated temperatures for an extended period of time.

This product was tested in the described apparatus with the results shown in Table IX.

TABLE IX

| | |
|---|---|
| Flow Rate: | 16 L/Hr |
| Heating Tube: | 15 Ft. length, ⅛" I.D. |
| Holding Tube Volume: | 0.0836 ml |
| Starting Temperature: | 35° C. |
| Heating Time: | 2.5 Sec. |
| Holding Time: | 0.18 Sec. |
| Cooling Time: | 2.1 Sec. |

| Peak Temperature | Log Reduction E. coli in Egg Product | Egg Protein Denaturation |
|---|---|---|
| 60° C. | 0.5 | No |
| 65° C. | 6.5 | No |
| 70° C. | 6.9 | No |
| 74° C. | 7.8 | No |
| 83° C. | 8.6 | No |
| 85° C. | 9.0 | Yes |

EXAMPLE 10

A suspension of liposomes containing an antibiotic compound was processed using the described apparatus for sterilization and destruction of spore-forming microorganisms.

| Initial Temperature | 4° C. |
|---|---|
| Flow Rate: | 12 L/Hr |
| Heating Rate: | 50° C./Sec |
| Peak Temperature: | 160° C. |
| Holding Time: | 0.016 sec |
| Final Temperaure: | 20° C. |

The suspension was seeded with $10^{10}$ spores of *B. stearothermophilus* bacterial spores. After processing at the parameters listed above, the physical integrity of the liposomes were intact, and the chemical activity of the antibiotic inside the liposomes were not negatively affected and the spores present were destroyed.

Liposome technology is used for drug delivery, immunization (delivery of antigens) and gene therapeutics (delivery of genetic material). Therefore, liposomes containing antibiotic and other drug and heat-sensitive compounds and materials may be processed to reduce the presence of the microorganism without affecting the antibiotic or other activity of the active ingredients therein.

What is claimed is:

1. A method for the high temperature, short time heating of a heat-sensitive liquid material which includes a heat-sensitive compound and microorganisms, which method comprises:
    (a) rapidly heating the heat-sensitive material at a rate of over about 50° C. per second for a heating time period to a preselected temperature of over about 60° C. and where the rate of reduction of the microorganism is greater than the rate of destruction of the heat-sensitive compound by the employment of microwave heating energy to provide a heated liquid material;
    (b) holding the said heated heat-sensitive material at the preselected temperature for a short holding time period;
    (c) rapidly cooling the heated heat-sensitive material to a preselected lower temperature for a cooling time period to provide a cooled heat-sensitive material;
    (d) circulating the heat-sensitive material while rapidly heating, holding and rapidly cooling the heat-sensitive material; and
    (e) the heating, holding and cooling time periods not greater than about 1.0 seconds and sufficiently short so as not to effect substantially the desirable properties of the heat-sensitive material, but sufficient for the desired reduction of the microorganism in the heat-sensitive material.

2. The method of claim 1 which includes adding a dielectric enhancing additive to the heat-sensitive material in an amount to increase the dielectric constant and enhance the heating rate.

3. The method of claim 2 which includes removing at least a portion of the added dielectric enhancing additive from the cooled heat-sensitive material.

4. The method of claim 2 which includes adding to the heat-sensitive material a dielectric enhancing additive of an ionic salt in an amount of about 0.1% to 10% by weight of the heat-sensitive material.

5. The method of claim 1 which includes heating the heat-sensitive material to a temperature of about 60° C. to 95° C. for a holding time period of less than about 0.05 seconds.

6. The method of claim 1 which includes heating the heat-sensitive material to a selected temperature of about 80° C. for a total heating, holding and cooling time period of less than about 0.5 seconds.

7. The method of claim 1 wherein the heat-sensitive liquid material comprises a biological fluid selected from the group consisting of body fluids, mother's milk, vaccines, fermentation broths and microbiological and cell media.

8. The method of claim 7 wherein the biological fluid comprises blood plasma or serum and which includes heating the blood plasma or serum to a selected temperature of over about 65° C. to 80° C. for a holding time period of less than about 0.05 seconds.

9. The method of claim 1 which includes heating the heat-sensitive material at a rate of about 50° C. to 8,000° C. per second.

10. The method of claim 1 which includes rapidly cooling the biological fluid to a temperature of less than about 30° C.

11. The method of claim 1 which includes circulating the heat-sensitive material at a flow rate of about 3 to 25 liters per hour with a hold-up volume of less than about 0.5 liters.

12. The method of claim 1 wherein the heat-sensitive material comprises an egg product.

13. The method of claim 1 wherein the heat-sensitive material comprises a suspension containing a drug.

14. The method of claim 1 wherein the holding time period is less than about 100 milliseconds.

15. The method of claim 1 which includes the reducing of up to about 20% of the microorganisms during the heating period.

16. The method of claim 1 which includes cooling the heat-sensitive material at a cooling rate of more than about 100° C. per second.

17. The method of claim 1 which includes selecting the selected temperature and the heating, holding and cooling time periods to affect a 6-log cycle reduction of the microorganism.

18. The method of claim 1 wherein the heat-sensitive compound comprises an enzyme.

19. The method of claim 1 wherein the heat-sensitive material comprises blood plasma or serum and the microorganisms include a virus, and the heat-sensitive compound comprises albumin, blood clotting factor VIII or blood clotting factor IX.

20. A method for the high temperature, short time heating of a blood plasma or serum to destroy a virus or infectious agent therein, which method comprises:
    (a) adding a dielectric salt additive to the blood plasma or serum to increase the dielectric constant of the blood plasma or serum to provide a dielectric constant of over about 90; and
    (b) rapidly heating the additive-containing blood plasma or serum to a selected temperature of about 60° C. for a holding period of time of less than about 0.1 seconds by microwave heating energy to destroy substantially the virus or infectious agent without substantially altering the albumin or the blood clotting factors VIII and IX of the blood plasma.

21. The method of claim 20 which includes rapidly heating the blood plasma or serum to the selected temperature for a holding time period of less than about 0.05 seconds and thereafter rapidly cooling the blood plasma or serum.

22. The method of claim 20 which includes circulating the blood plasma or serum while rapidly microwave heating and holding and cooling the blood plasma or serum and heating the blood plasma or serum to a sterilizing temperature of more than about 75° C. to provide a sterilized blood plasma or serum.

23. The method of claim 20 which includes separating from the blood plasma or serum at least a part of the dielectric salt additive.

24. A high temperature, short time heat process system for the rapid heating, holding and cooling of a heat-sensitive material to destroy undesirable agents therein without substantial alteration of other desirable heat-sensitive components or properties of the heat-sensitive material, which system comprises:
   (a) a source of heat-sensitive material to be heated;
   (b) microwave heating energy means to heat rapidly for a heating time period said heat-sensitive material from the said source at a rate of about 25° C. to 8000° C. per second to a preselected temperature of over about 60° C. for a holding time period of up to about 0.5 seconds to destroy undesirable agents in the heat-sensitive material without substantial alteration of other desirable heat-sensitive components or properties in the heat-sensitive material;
   (c) cooling means to cool rapidly the heated heat-sensitive material to a preselected cooler temperature at a rate of greater than 100° C. in a cooling time period to provide a cooled heat-sensitive material without substantial alteration of other desirable heat-sensitive components or properties in the heat-sensitive material;
   (d) circulating means to permit the flow of said heat-sensitive material from said source of heat-sensitive material and through said microwave heating energy means in a microwave heating relationship and through the said cooling means in a cooling relationship and to the means to recover the cooled heat-sensitive material;
   (e) pump means to pump said heat-sensitive material through said circulating means; and
   (f) means to recover the cooled heat-sensitive material.

25. The system of claim 24 which includes a source of dielectric enhancing additive for addition to the source of the heat-sensitive material in an amount sufficient to increase the dielectric constant of said heat-sensitive material to a dielectric constant of over about 90.

26. The system of claim 25 which includes a separation means to separate at least part of the dielectric enhancing additive from the cooled heat-sensitive material.

27. The system of claim 24 which includes a divert valve means in the circulating means to provide for the diversion and discard from the system of heat-sensitive material circulated through the microwave heating energy means in the event the microwave heating energy means fails to heat said material to the preselected temperature.

28. The system of claim 24 which includes a back pressure valve means positioned after cooling means in the circulating means to prevent the vaporization in the system of the heated heat-sensitive material.

29. The system of claim 24 wherein the source of heat-sensitive material comprises a biological fluid.

30. The system of claim 24 wherein the source of heat-sensitive material comprises blood plasma or serum.

31. The system of claim 24 wherein the source of heat-sensitive material comprises a suspension of a drug with a contaminating microorganism as an undesirable agent.

32. The system of claim 24 wherein the source of a heat-sensitive material comprises an egg product with a contaminating microorganism as an undesirable agent.

33. A method for the pasteurization of an infectious agent and proteinaceous-containing, heat-sensitive, biological fluid which method comprises:
   (a) rapidly heating the biological fluid by microwave energy at a rate of over about 50° C. per second to a preselected pasteurization temperature of greater than about 60° C. for a time period of less than about 0.050 seconds;
   (b) rapidly cooling the heated biological fluid to a preselected lower temperature of less than 50° C.; and
   (c) recovering a pasteurized biological fluid substantially free of the infectious agent and without substantial change in the proteinaceous material of the biological fluid.

34. The method of claim 33 wherein the pasteurization temperature is greater than about 75° C.

35. The method of claim 33 wherein the biological fluid comprises blood plasma.

36. The method of claim 33 wherein the proteinaceous material is selected from the group consisting of immunoglobins, factor VIII and factor IX.

37. The method of claim 33 wherein the infectious agent is selected from the group consisting of: bacteria, myoplasma and virus.

38. The method of claim 33 wherein the preselected pasteurization temperature comprises from about 65° C. to 95° C.

39. The method of claim 33 wherein the rate of cooling the heated biological fluid is greater than about 10° C. per second.

40. The method of claim 33 which includes cooling the heated biological fluid to a temperature less than about 30° C.

41. The method of claim 33 which includes employing a microwave energy source having a power of about 500 to 6000 watts.

42. The method of claim 33 which includes circulating the biological fluid through a microwave permeable heating zone and a cooling zone.

43. The method of claim 33 which includes adding an inert dielectric-enhancing additive to the biological fluid to increase the dielectric constant of the biological fluid.

* * * * *

UNITED STATES PATENT AND TRADEMARK OFFICE
CERTIFICATE OF CORRECTION

PATENT NO. : 4,975,246

DATED : December 4, 1990

INVENTOR(S) : Stanley E. Charm

It is certified that error appears in the above-identified patent and that said Letters Patent is hereby corrected as shown below:

Column 14, line 46, delete "10°" and insert --100°--.

Signed and Sealed this

Seventh Day of April, 1992

Attest:

HARRY F. MANBECK, JR.

*Attesting Officer*  *Commissioner of Patents and Trademarks*